US010758202B2

United States Patent
Daerr et al.

(10) Patent No.: US 10,758,202 B2
(45) Date of Patent: Sep. 1, 2020

(54) SPECTRAL IMAGING PHANTOM AND METHOD

(71) Applicant: KONINKLIJKE PHILIPS N.V., Eindhoven (NL)

(72) Inventors: Heiner Daerr, Hamburg (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 131 days.

(21) Appl. No.: 15/758,367

(22) PCT Filed: Sep. 22, 2016

(86) PCT No.: PCT/EP2016/072570
§ 371 (c)(1),
(2) Date: Mar. 8, 2018

(87) PCT Pub. No.: WO2017/050914
PCT Pub. Date: Mar. 30, 2017

(65) Prior Publication Data
US 2018/0249983 A1 Sep. 6, 2018

(30) Foreign Application Priority Data

Sep. 23, 2015 (EP) .................................. 15186385

(51) Int. Cl.
*A61B 6/00* (2006.01)
*A61B 6/03* (2006.01)
(Continued)

(52) U.S. Cl.
CPC .............. *A61B 6/583* (2013.01); *A61B 6/032* (2013.01); *G09B 23/286* (2013.01); *G09B 23/30* (2013.01)

(58) Field of Classification Search
CPC ...... A61B 6/032; A61B 6/583; G09B 23/286; G09B 23/30
See application file for complete search history.

(56) References Cited

U.S. PATENT DOCUMENTS 4,233,507 A    11/1980   Volz
4,922,915 A *    5/1990   Arnold .................. A61B 6/583
                                                378/18

(Continued)

FOREIGN PATENT DOCUMENTS

WO    2008/046498    4/2008
WO    2014181315    11/2014

OTHER PUBLICATIONS

Herrmann, et al., "Performance simulation of an x-ray detector for spectral CT with combined SI and Cd[Zn]Te detection layers"; Physics in Medicine and Biology; vol. 55, No. 24; Nov. 26, 2010.

(Continued)

*Primary Examiner* — Marcus H Taningco
(74) *Attorney, Agent, or Firm* — Larry Liberchuk

(57) ABSTRACT

The present invention is directed towards spectral imaging, wherein a dedicated spectral imaging phantom is scanned with a spectral x-ray device to obtain spectral imaging data of the spectral imaging phantom. Said imaging data of the spectral imaging phantom is used as input for obtaining improved further imaging data of a subject of which a spectral scan is performed subsequent to or simultaneous with the spectral scan of the spectral imaging phantom. Improved further imaging data may be obtained by using the spectral phantom imaging data as input for imaging data correction, for providing a recommendation and/or for further data processing.

19 Claims, 4 Drawing Sheets

(51) Int. Cl.
*G09B 23/28* (2006.01)
*G09B 23/30* (2006.01)

(56) References Cited

U.S. PATENT DOCUMENTS

| | | | |
|---|---|---|---|
| 2008/0137803 A1 | 6/2008 | Wu | |
| 2008/0226017 A1 | 9/2008 | Altman | |
| 2010/0167251 A1* | 7/2010 | Boutchko | A61B 5/416 |
| | | | 434/267 |
| 2011/0249879 A1 | 10/2011 | Wu | |
| 2012/0076259 A1 | 3/2012 | Holt | |
| 2012/0155617 A1 | 6/2012 | Dutta | |
| 2016/0278735 A1* | 9/2016 | Franke | A61B 5/055 |
| 2018/0035970 A1* | 2/2018 | Avila | A61B 6/032 |
| 2018/0047303 A1* | 2/2018 | Groenewald | A61B 6/502 |

OTHER PUBLICATIONS

Alvarez, et al., "Estimator for photon counting energy selective x-ray imaging with multibin pulse height analysis"; Med. Phys. 38 (5), May 2011.

Roessl, et al., "K-edge imaging in x-ray computed tomography using multi-bin photon counting detectors"; Phys. Med. Biol. 52 (2007) 4679-4696.

Schirra, et al., "Towards In-vivo K-edge Imaging Using a New Semi-Analytical Calibration Method"; Proc. SPIE 9033, Medical Imaging 2014: Physics of Medical Imaging, 90330N (Mar. 19, 2014).

Schlomka, et al., "Experimental feasibility of multi-energy photon-counting K-edge imaging in pre-clinical computed tomography"; Phys. Med. Biol. 53 (2008) 4031-4047.

* cited by examiner

SPECTRAL IMAGING PHANTOM AND METHOD

CROSS REFERENCE TO RELATED APPLICATIONS

This application is the U.S. National Phase application under 35 U.S.C. § 371 of International Application No. PCT/EP2016/072570, filed Sep. 22, 2016, published as WO 2017/050914 on Mar. 30, 2017, which claims the benefit of European Patent Application Number 15186385.9 filed Sep. 23, 2015. These applications are hereby incorporated by reference herein.

FIELD OF THE INVENTION

The present invention relates to a spectral imaging phantom, a spectral imaging system and towards a spectral imaging method using the spectral imaging phantom.

BACKGROUND OF THE INVENTION

One of the advantages of spectral imaging, such as 2D or 3D x-ray imaging, for instance spectral Computed Tomography (CT), is that it may provide quantitative material images after material decomposition. For the material decomposition various methods may be contemplated, including, for instance, a dimensional look-up table approach (for instance known from Alvarez, R. E, Estimator for photon counting energy selective x-ray imaging with multi-bin pulse height analysis, Med. Phys., 2011, 38, 2324-2334), a theoretical forward model (for instance known from Roessl, E., Proksa, R, K-edge imaging in x-ray computed tomography using multi-bin photon counting detectors, Phys. Med. Biol., 2007, 52, 4679-4696) or application of a semi-analytic approach (for instance known from Schirra, C. et al, Towards In-vivo K-edge Imaging Using a New Semi-Analytical Calibration Method, Proc. SPIE 9033, Medical Imaging 2014: Physics of Medical Imaging, 90330N, 19 Mar. 2014).

These and other known methods face the same problem that the outcome becomes distorted in case the status of the scanner and object of interest differ from the status during calibration. The status of the detector may change due to polarization of the sensor or the x-ray spectrum from the tube might change, e.g. due to heating during scanning An approach utilizing a look-up table (even with three or more materials) suffers from the fact that the human body does not consist exactly out of the materials used in the calibration. Artefacts like rings, bands, or cross-talk between the material images occurs due to the energy dependency of the attenuation of different materials, the different detector spectral responses and x-ray spectrum for different detector parts. It is likely that spectral forward models or semi-analytical approach never exactly matches the measurement. Scatter has a spectral footprint and changes the detected counts differently in different bins. This complicates the model even further. The mismatch in prediction and measurement produces cross-talk and artefacts in the material images. A better forward model or semi-analytical approach reduces the artefacts but it is not clear if the ultimately resulting images quality is good enough for quantitative medical imaging.

Besides the previously described systematic errors, the quality of the (temporal) stability of detector might frequently make a new spectral calibration necessary. It would be desirable to assess the status of the CT scanner in order to recommend a spectral calibration.

All mentioned image artefacts depend on the chosen scan protocols, especially on the x-ray tube voltage. After best processing, it would be preferable to provide a user, such as an operator or a physician, in a qualitative and a quantitative way about the remaining errors in the images. In best case the user is informed about the absence of significant errors.

US2012/0155617 A1 discloses a spectral CT calibration phantom that has inserts which allow for filling with a liquid) material that mimic the attenuation of different parts of a body.

WO2008/046498 A1 discloses a calibration method for two or more spectra tomography to determine material decomposition coefficients.

SUMMARY OF THE INVENTION

It is an object of the present invention, amongst others, to overcome the previously mentioned problems.

In the present invention this is achieved by a spectral imaging phantom comprising a phantom body that includes a low attenuation material and at least a first insert comprising a material with a first Compton scatter and a first photo-electric absorption and a second insert with a second Compton scatter and a second photo-electric absorption, wherein a ratio of the first photo-electric absorption and the first Compton scatter is selected to be different from a ratio of the first photo-electric absorption and the first Compton scatter. Such an imaging phantom simulates the response of a subject, such as a human body. In a preferred embodiment Spectral imaging phantom according to claim 1, wherein the first insert and the second insert have substantially the same attenuation profile, preferably exactly the same attenuation profile, which allows for distinguishing even more precise between the spectral properties of different inserts, irrespective of the attenuation of the inserts themselves. In a preferred embodiment the low attenuation material is a water equivalent material.

In a preferred embodiment at least one further insert comprising a material comprising or corresponds to the contrast agent at a further concentration, a further contrast agent at a first and/or a further concentration and/or a further material with a further Compton scatter and a further photo-electric absorption, including combinations thereof. As such, the response of more sections of the subject may be simulated.

In a preferred embodiment the first (and further) inserts are chosen such that they mimics attenuation characteristics of a part of a subject to be imaged, for instance the first and/or further inserts comprise a material comprising or corresponding to iodine or gadolinium contrast agents in one or more different concentrations or Teflon, PMMA, Polycarbonate, Polyethylene, Sodium Hydrogen Phosphate or Potassium Hydrogen Phosphate.

In a preferred embodiment the phantom body has flat shape or an arched shape, such that it can be placed under, on or over a subject to be scanned. Preferably the shape is elongated to cover a larger area, for instance a full subject or at least a part of interest of the subject. Also it might be more comfortable for a human to be ingredients.

In a further preferred embodiment the phantom body and inserts are solid. This allows for not having to fluidly isolate the inserts and the body to prevent leakage.

In a further embodiment the inserts are permanently fixed in the phantom body. This allows for ease of use, since no preparation is necessary before each procedure, which also allows for better reproducibility between procedures.

Embodiments of the present invention are further directed towards a spectral imaging system comprising a spectral x-ray imaging device, preferably a spectral computed tomography imaging device, and a spectral imaging phantom according to the invention. The spectral imaging phantom is preferably embedded in a subject support of the spectral x-ray imaging device, which allows for ease of use and a fixed position that allows for always generating the same data with respect to the imaging device.

Embodiments of the present invention are further directed towards a spectral imaging method including the steps of inserting a spectral imaging phantom according to present invention in an examination region of a computed tomography imaging device, performing a spectral computed tomography scan including at last a scan of the spectral imaging phantom, thereby obtaining spectral imaging data of at least the spectral computed tomography phantom and using the obtained imaging data of the spectral computed tomography phantom as input for obtaining improved further imaging data of a subject of which a spectral computed tomography scan is performed subsequent to or simultaneous with the spectral computed tomography scan of the spectral imaging phantom. Preferably the spectral imaging phantom is used as input for obtaining improved image data by using it as input for imaging data correction, for providing a recommendation and/or for further data processing. Imaging data of the spectral phantom may be used to improve image quality or reliability which assist physicians in their diagnosis, for instance of an area of interest of the subject.

In a preferred embodiment the spectral scan of the subject is performed simultaneously with the spectral scan of the spectral phantom. As such, imaging data of the subject and the phantom are taken at the same time and data from the phantom is therefore much better reflects actual irradiation conditions received by the subject.

In a preferred embodiment the spectral imaging method further comprises the steps of quantifying a crosstalk in material decomposition of the imaging data, correcting the obtained image data for the quantified crosstalk; and, optionally, determining at least one system parameter and use said at least one system parameter in the correction of the quantified crosstalk. By correcting for the crosstalk, more reliable images are obtained.

In a preferred embodiment the spectral imaging method further comprises the steps of comparing the obtained imaging data of the spectral phantom with reference imaging data, said reference data comprising theoretical data, data measured with other sources, previously measured data of a subject to be imaged, and/or data of the spectral phantom obtained during a previous scan of the spectral phantom, preferably a previous scan shortly after a latest calibration procedure; and providing a recommendation for a special action, for instance a recommendation for performing a new calibration when a difference between the obtained imaging data and the imaging data obtained during or shortly after the latest calibration exceeds a predetermined threshold. A user may decide to recalibrate the imager and thereby improve reliability of subsequently obtained subject image data.

In a preferred embodiment the spectral imaging method further comprises the step of reconstructing the imaging data by using the obtained imaging data of the spectral imaging phantom as input for a reconstruction algorithm, preferably an iterative reconstruction algorithm. In this way 'calibration' data from the phantom is used in the reconstruction of the image, which helps to improve the reliability of the modeled imaging data.

Figure 1A:
FIG. 1A-E show five schematically depicted embodiments for a spectral calibration phantom according to the present invention.

The invention may take form in various components and arrangements of components, and in various process operations and arrangements of process operations. The drawings are only for the purpose of illustrating preferred embodiments and are not to be construed as limiting the invention. To better visualize certain features may be omitted or dimensions may be not be according to scale.

DETAILED DESCRIPTION OF EMBODIMENTS

The present invention is explained using CT imaging as an example, but the present invention would also be suitable, with modifications a skilled person would know how to implement, for other spectral (x-ray) imaging systems, such as 2D or 3D (e.g. C-arm) spectral x-ray imaging systems.

Calibration phantoms for calibrating x-ray imagers, such as CT systems, are known. Phantoms are artificial constructs with precisely known attenuation properties, which are normally scanned (often with a stationary) gantry to determine detector response properties in a controlled, reproducible manner for calibration purposes or detector diagnostics.

Known CT phantoms are not optimal for use with spectral CT, since the phantom must simulate the response of the human body for Compton scatter and photo-electric absorption at all x-ray wavelengths used in the scan. This may be achieved by equipping the spectral phantom body 10 with at least two inserts, each selected to have a different ratio between photo-electric effect and compton scattering. This allows for optimizing the spectral information. In a preferred embodiment the at least two inserts are selected to have the same attenuation characteristics, but with a different ratio between photo-electric effect and compton scattering. This allows for distinguishing the spectral information irrespective of the attenuation.

The proposed spectral phantom 10 preferably comprises a bulk of a low attenuation material and at least one insert positioned therein.

It is preferable to use materials for the bulk and the inserts that mimic attenuation characteristics of one or more parts of a patient's body, such as organs, bones, or body fluids. The low attenuation material is preferably a water equivalent material, such as Delrin. As such the detector response is determined using a phantom that mimics a patient to be imaged, which therefore more likely results in a scanner that is optimally calibrated for the patient's body.

The inserts may be constructed using frequently used contrast agents, such as iodine or gadolinium, at different concentrations. The inserts may comprise actual contrast agent materials or 'contrast agent-like' materials that respond the same or very similar to contrast agents. As a non-limiting example, the spectral phantoms 10 depicted in FIGS. 1A to 1E have a first insert CA-1-1 comprising iodine at a first concentration, a second insert CA-1-2 comprising iodine at a second concentration, a third insert CA-2-1 comprising gadolinium at a first concentration and a fourth insert CA-2-2 comprising gadolinium at a second concentration. More or less species of contrast agents and/or concentrations may also be used.

Alternatively or additionally, inserts may also be constructed using materials with a different ration of photo-electric absorption and Compton scatter. As a non-limiting example, the spectral phantoms 10 shown in FIGS. 1A to 1E comprise six of such inserts with a different ration of photo-electric absorption and Compton scatter. These inserts P-C-1, P-C-2, P-C-3, P-C-4, P-C-5, P-C-6 respectively comprise polytetrafluoroethylene (Teflon), polymethyl methacrylate (PMMA), polycarbonate (PC), polyethelene (PE), sodium hydrogen phosphate ($Ca_2HPO_4$) and potassium hydrogen phosphate ($K_2HPO_4$). Less, other and more materials may be contemplated as well.

Preferably the spectral phantom according to the present invention comprises at least one, but preferably more, contrast agent inserts and at least one, preferably more, photo-electric absorption and Compton scatter inserts.

The spectral phantom 10 of the present invention may have any shape that fits in a spectral scanner. The spectral phantom of the present invention may be scanned together with a subject 1, such as a patient, preferably close to an area of interest 2 of the subject. The shape and the design of the phantom may be adapted to accommodate this. The area of interest may in the context of the invention also be understood be a three-dimensional volume in the subject, such as an organ or a delimited section of the patient.

In a preferred embodiment he phantom body and inserts are solid, such as crystalline materials, (plastic) foils, etcetera. Known phantoms often use liquid materials, that may cause leakage resulting in severe damage to the phantom, the imaging system or may harm a patient.

In a further embodiment the inserts are permanently fixed in the phantom body. Many known inserts need to be prepared (particularly fluid inserts), which is cumbersome and needs to be done very precise. Using fixed inserts allows for ease of use, since no preparation is necessary before each procedure anymore, which also allows for better reproducibility between procedures. Obviously, the inserts must be chosen such that they are well-tuned for a wide range of subjects and objects of interest. It may be necessary to keep various phantoms in stock with different, permanently fixed inserts.

Figure 1B:
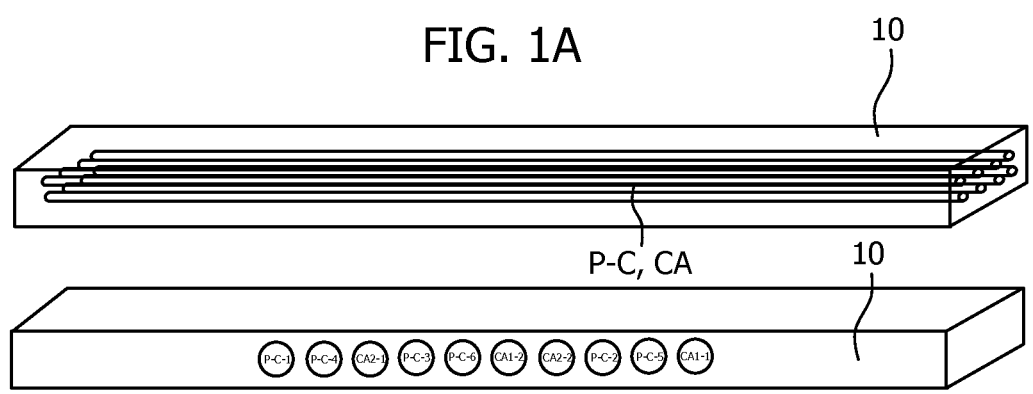

FIGS. 1A and 1B show a spectral phantom 10 that may be placed under a subject to be scanned. The phantom of FIG. 1A is arched, which improves patient comfort, while the phantom of FIG. 1B is flat, which is easier to construct. Both these embodiments show an elongated shape, which allows the subject to lie on top of it. More compact solutions are possible as well, which reduces manufacturing cost and storage space requirements, but these may hinder patient comfort. Inserts (P-C, CA) may be positioned within the phantom body 10 in various manners, either grouped together or spaced apart. Preferably the inserts (P-C, CA) are positioned along the main length axis of the phantom, which allows for imaging all inserts in one imaging slice in a CT imager (as shown in the top images of FIGS. 1A and 1B). But it is also possible to have the inserts spread across the phantom body or in the width axis (as shown in the bottom images of FIGS. 1A and 1B).

Figure 2A:
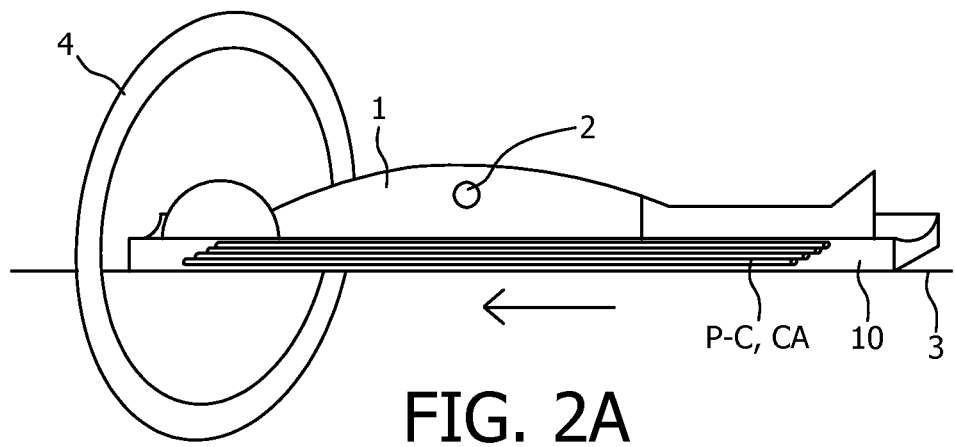
FIG. 2A-E show various embodiments of a spectral calibration phantom according to the present invention depicted on a subject to be imaged.
Figure 2B:
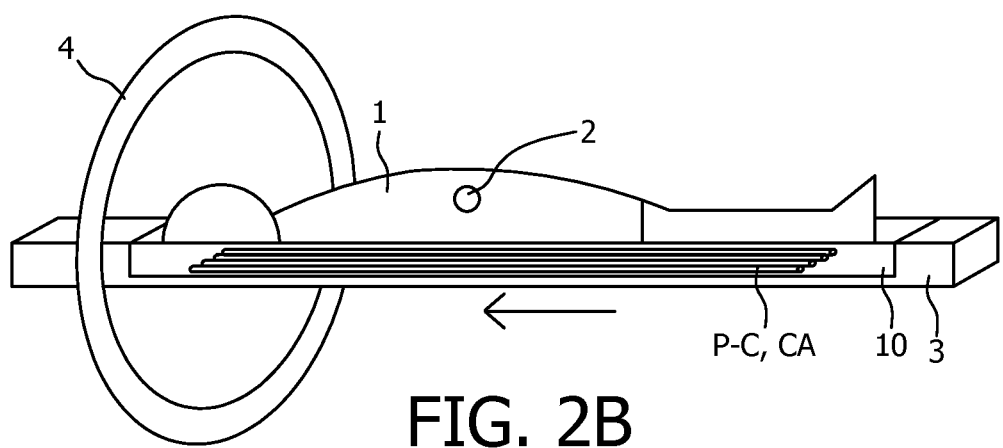

An advantage of placing the phantom under the subject is that, when scanned together with the subject, a position of the phantom is not influenced by patient movement. FIGS. 2A and 2B show a spectral imaging system according to the present invention using the embodiments of respectively FIGS. 1A and 1B in an imaging procedure together with a patient. The embodiments of FIGS. 2A and 2B show the phantom embedded into the patient support of an imaging device, which allows for a particularly compact design. Furthermore it always has exactly the same position for each subsequent scan.

Figure 1C:
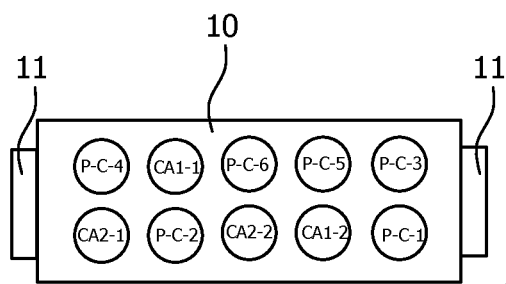
Figure 1E:
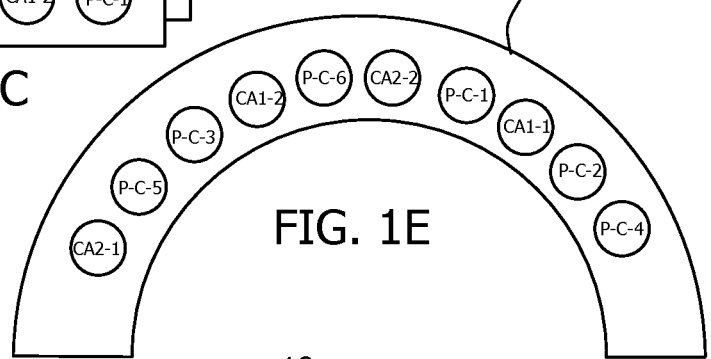
Figure 1D:
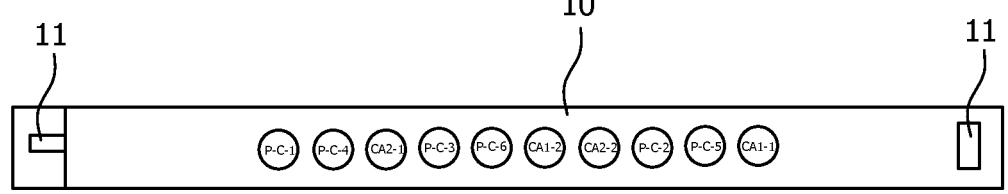

FIGS. 1C, 1D and 1E show embodiments that are placed on or above a subject to be scanned. An advantage of this is that, when scanned together, no attenuation of radiation within the patient has occurred, so the phantom receives a full emitted dose of radiation. Also, these embodiments may be positioned near an area of interest within the subject.

Figure 2C:
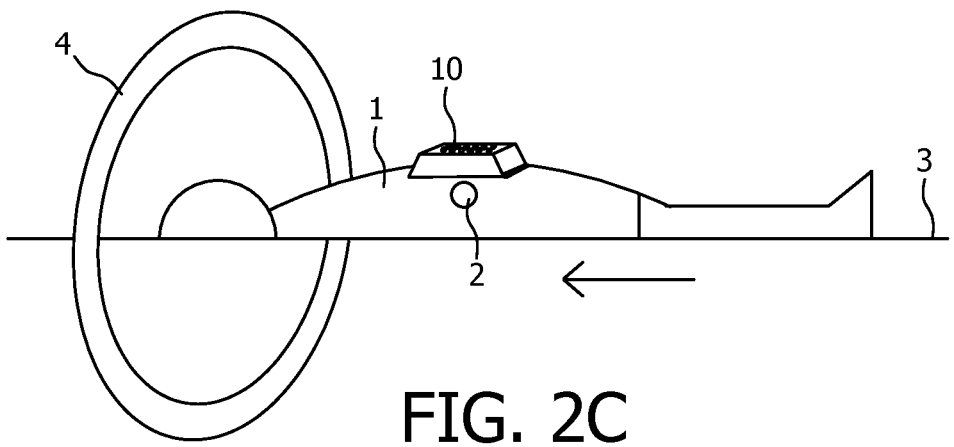

FIG. 1C shows a spectral phantom 10 with a block-like shape which may be attached on the body of or close of a patient 2 with attachment means 11, as is shown in FIG. 2C for a patient 2 lying on a patient support 3 about to be moved through a gantry 4 of a CT scanner for a scan. The attachment means 11 may comprise clips, tape or any other known attachment means. This embodiment is depicted as a rectangular block, but it may also have different shapes, for instance such as a rectangular, circular or elliptical plate or as an arch or a ring.

Figure 2D:
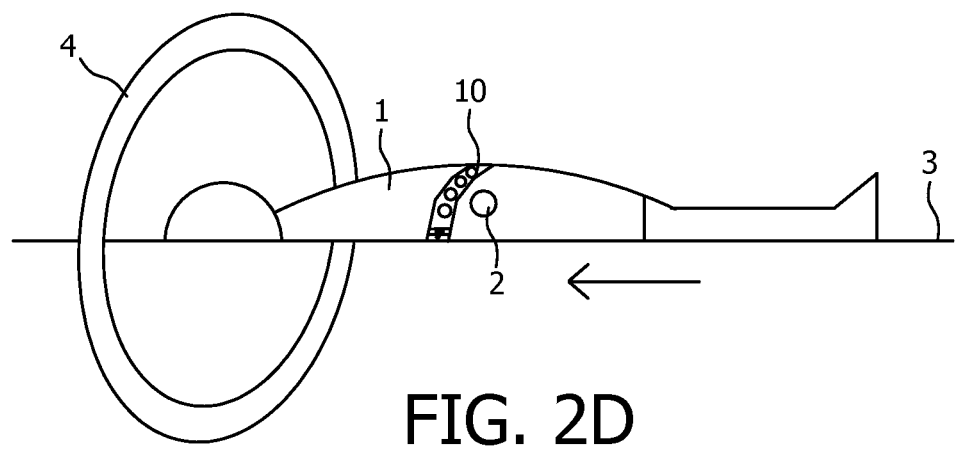

FIG. 1D depicts a spectral phantom 10 that is incorporated in a belt, which may be tied around a subject 2 to be scanned, as is shown is FIG. 2D. The belt may be closed using attachment means 11, which may take any form, such as belt buckles, buttons, Velcro, etc. An advantage is that there is less chance of the spectral phantom sliding off the patient compared to the embodiment of FIG. 1C, for instance for particularly mobile subjects, such as children, animals or physically or mentally challenged subjects. Also it is potentially less uncomfortable than the embodiment of FIG. 1C when attached directly to the skin of the patient. Also, it may be attached tight to the patient 2, and therefore potentially closer to the area of interest 2.

Figure 2E:
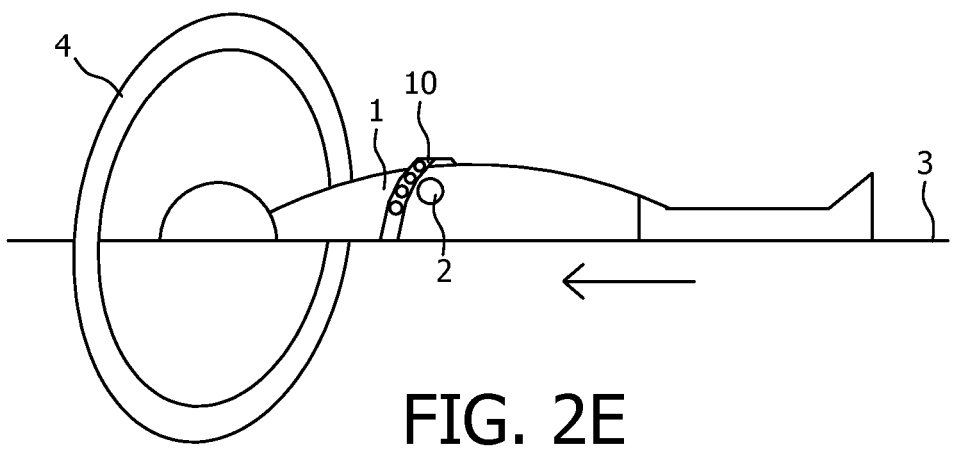

FIG. 1E shows an arch-shaped spectral phantom 10 that may be positioned over the subject 2 to be scanned, as is shown in FIG. 2E. An advantage of this compact embodiment is that it is always at the same relative distance from the detector and it does not need to be attached to the patient 2 and is therefore not influenced by patient movement. Also, it receives direct unhindered emitted radiation without radiation attenuated by the subject.

In all described embodiments the spectral phantom 10 and/or subject 1 may be optimally placed, such that the data obtained from scanning the phantom 10 corresponds spatially with the area of interest 2.

Figure 3:
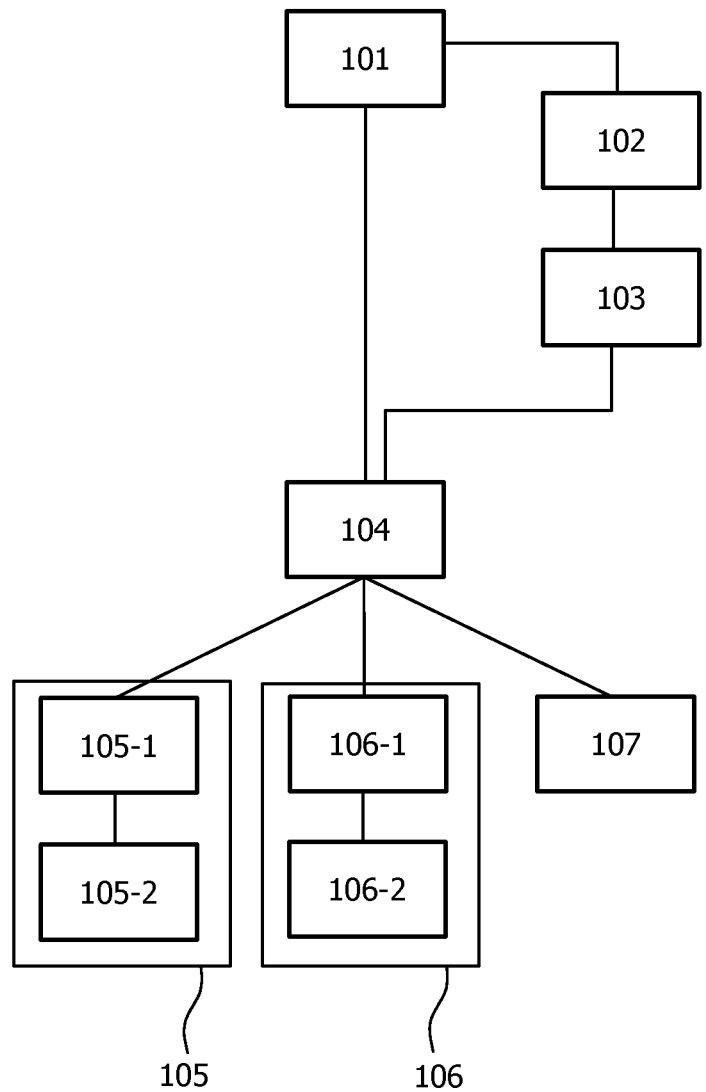
FIG. 3 shows a flowchart illustrating a spectral imaging method according to the present invention.

FIG. 3 depicts a flow chart of a spectral scanning method according to the present invention. In step 101 a phantom according to the present invention is placed in a CT device, to be scanned in spectral scanning step 104 to obtain spectral imaging data of the spectral phantom. In context of the present invention the phrases 'placed in a device' or inserted in an device' may be interpreted as being placed inside an examination region of the gantry, but also includes being placed on, in or over a support of the imaging device outside the examination region. During scanning 104 the phantom may be stationary within the gantry or may be moved translated through the gantry, while the gantry may also be stationary or it may be rotating.

It is particularly advantageous to scan 104 the phantom together with the subject to be scanned, preferably close to the area of interest of the subject. To achieve this the subject to be scanned is also placed 102 in the CT device and the spectral phantom is positioned 103 on or near the subject, preferably near the area of interest. This includes placing the phantom on a desired position, but also includes positioning the patient relative to a (stationary) phantom. The term 'near the area of interest' in context of the present invention means close to the area of interest, preferably as close to the area of interest as physically possible or comfortable, while also not hindering the scan of the area of interest. This may in some case mean next to, under, on or over the area of interest. By scanning the phantom and the subject together the imaging data for the spectral phantom and the further spectral imaging data of the subject is temporarily and spatially optimally aligned.

After the scanning step 104 the spectral imaging data of the phantom may be used to determine detector response for a potential calibration or diagnostics step 108, as is the common use for calibration phantoms.

However, in the present invention the phantom is not a calibration phantom in the traditional sense, but an imaging phantom in which imaging data is specifically used 105, 106, 107 to improve further image data, for instance of a subject to be scanned simultaneously with or subsequent to the scan of the spectral phantom. The further image data may be improved by the spectral imaging data of the phantom by using 105 the spectral imaging data as input for data correction of the further imaging data, or by using 106 the spectral imaging data of the spectral phantom to generate a recommendation to a user regarding a scan to generate the further image data, or by using 107 the spectral imaging data of the phantom as additional input for image reconstruction of the further spectral imaging data.

Using 105, 106, 107 the spectral imaging data may for instance be done in various manners, for instance by using systematic cross-talk or bias that is inherent in any material decomposition method for spectral CT imaging. Systematic errors in the material decomposition of spectral CT data manifests in image artefacts like rings or bands and in cross-talk between the material images. These artefacts can also arise or change during scanning The systematic cross-talk inherent in the material decomposition of the spectral imaging data of the phantom may be quantified 105-1 and dedicated correction algorithms may then be applied as an input parameter to correct 105-2 for the quantified cross-talk in the further imaging data. Especially if the imaging data of the phantom and the further imaging data were acquired simultaneously, a relevant and accurate correction of the further imaging data may be achieved. Additionally changes of some system parameters may also be detected and appropriate input parameter(s) for the correction algorithm may be adapted to achieve even further optimized further imaging data.

The decomposed material images of the spectral CT phantom of the current scan may be compared 106-1 to images acquired right after the last spectral calibration. In case the differences between the images or the errors in the latest images are too large (measured in appropriate metrics), a special action may be recommended 106-2, for instance a suggestion to perform a new energy calibration, switching the high voltage on an off or performing a material calibration or other spectral calibrations. As such, the CT device is optimized for scanning the subject and improved further image data of a subject may be obtained.

Alternatively or additionally, the residual amount of cross-talk or absolute errors of the CT values in the final material images can be assessed by comparing 106-1 the outcome of the spectral CT phantom with the ground truth and providing the results 106-2, e.g. by displaying them, for supporting the viewer in reading the images and potentially to prompt the viewer to take an action to obtain improved further image data.

The decomposed material images of spectral CT phantom may also be used 107 during iterative reconstruction to tune the parameter for each slice. For reference, the standard iterative multi-channel reconstruction may be denoted by equation (1):

$$\Delta^2 = \sum_i \left\| C_i^{-\frac{1}{2}} \left[ \begin{pmatrix} Ap \\ AS \\ Ak \end{pmatrix} - \begin{pmatrix} m_{i,p} \\ m_{i,S} \\ m_{i,k} \end{pmatrix} \right] \right\|^2 + \lambda R(p, S, k) \quad (1)$$

In equation (1) i indexes all projections, $A_i$ is the forward projection operator for projection angle i; p, S, and k are the photoelectric, the scatter, and the k-edge material image, respectively, and $m_{i,p}$, $m_{i,S}$ and $m_{i,k}$ are the decomposed, measured line integrals for projection direction i. The matrix $C_i$ is the noise covariance matrix of the projections $m_{i,p}$, $m_{i,S}$, and $m_{i,k}$. Finally, R is a regularization term weighted with a regularization parameter $\lambda$(lambda) that enforces some additional constraints, e.g. smoothness, in order to stabilize the solution. It was empirically found that the crosstalk can be reduced by a heuristic linear model, such as shown in equation (2):

$$\begin{pmatrix} \tilde{m}_{i,p} \\ \tilde{m}_{i,S} \\ \tilde{m}_{i,k} \end{pmatrix} = T_i \begin{pmatrix} m_{i,p} \\ m_{i,S} \\ m_{i,k} \end{pmatrix} \quad (2)$$

For instance, if the linearly transformed measurements are used for reconstruction. The spectral "instability" of the system is reflected in the fact that the transformation matrix T depends on the projection index. Nevertheless, T is close to the unity matrix. Now with the proposed phantom being inside the field of view, it becomes possible to estimate the elements of T during iterative reconstruction by optimizing the cost function also with respect to the free parameters of $T_i$, as is shown in equation (3):

$$\Delta^2 = \sum_i \left\| C_i^{-\frac{1}{2}} \left[ \begin{pmatrix} Ap \\ AS \\ Ak \end{pmatrix} - T_i \begin{pmatrix} m_{i,p} \\ m_{i,S} \\ m_{i,k} \end{pmatrix} \right] \right\|^2 + \quad (3)$$

$$\lambda_1 R_1(p, S, k) + \lambda_2 R_2(T) + \lambda_3 \left\| \begin{pmatrix} M_p \\ M_S \\ M_k \end{pmatrix} - \begin{pmatrix} Q_p \\ Q_S \\ Q_k \end{pmatrix} \right\|^2$$

An additional regularization term $R_2$ is added in the cost function (which takes as argument all $T_i$ matrices) in order to include prior knowledge about T. Possible prior knowledge to be included may contain temporal smoothness, row-wise normalization symmetry, distance to the unity matrix, and alike. The last term that is added in the cost function is prior knowledge about the phantom. This is included in form of a mask operator M, which masks the location of the phantom, and in the form of the a-priori known values $Q_p$, $Q_S$, and $Q_k$, of the photo-electric effect, the Compton scattering, and the k-edge material within the phantom respectively.

Other known reconstruction algorithms may be similarly adapted used to obtain improved images from the further image data. Computer program products may execute the algorithms.

While the invention has been illustrated and described in detail in the drawings and foregoing description, such illustration and description are to be considered illustrative or exemplary and not restrictive; the invention is not limited to the disclosed embodiments. For instance, the spectral imaging phantom and spectral imaging method were explained using spectral CT imaging, but a skilled person would know how to adapt the invention for use in other spectral imaging methods, e.g. 2D or 3D spectral x-ray imaging.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims and description. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A spectral imaging phantom for a spectral x-ray imaging device, the spectral imaging phantom comprising a phantom body that comprises:
   a bulk of low attenuation material;
   a first insert positioned in the bulk, the first insert comprising a material comprising or corresponding to a material with a first Compton scatter and a first photo-electric absorption with respect to a scan energy of the spectral x-ray imaging device; and
   a second insert positioned in the bulk, the second insert comprising a material comprising or corresponding to a material with a second Compton scatter and a second photo-electric absorption with respect to the scan energy,
   wherein the first insert and the second insert have substantially the same attenuation profile with respect to the scan energy, and
   wherein a ratio of the first photo-electric absorption and the first Compton scatter is selected to be different from a ratio of the second photo-electric absorption and the second Compton scatter.

2. The spectral imaging phantom according to claim 1, comprising at least one further insert comprising a material comprising or corresponding to a contrast agent at a first concentration, a further contrast agent at a first and/or a further concentration and/or a further material with a further Compton scatter and a further photo-electric absorption, comprising combinations thereof.

3. The spectral imaging phantom according to claim 2, wherein the at least one further insert comprise iodine or gadolinium contrast agents in one or more different concentrations and/or Teflon, PMMA, Polycarbonate, Polyethylene, Sodium Hydrogen Phosphate or Potassium Hydrogen Phosphate.

4. The spectral imaging phantom according to claim 2, wherein the first insert is chosen such that it mimics attenuation characteristics of a part of a subject to be imaged; and for the spectral imaging phantom, wherein the at least one further insert is chosen such that it mimics attenuation characteristics of a part of the subject to be imaged.

5. The spectral imaging phantom according to claim 1, wherein the first insert comprises a material comprising or corresponding to iodine or gadolinium contrast agents in one or more different concentrations or Teflon, PMMA, Polycarbonate, Polyethylene, Sodium Hydrogen Phosphate or Potassium Hydrogen Phosphate.

6. The spectral imaging phantom according to claim 1, wherein the phantom body has flat shape or an arched shape, such that it can be placed under, on or over a subject to be scanned.

7. The spectral imaging phantom according to claim 1, wherein the phantom body has an elongated shape.

8. The spectral imaging phantom according to claim 1, wherein the phantom body and inserts are solid.

9. The spectral imaging phantom according to claim 1, wherein the inserts are permanently fixed in the phantom body.

10. A spectral imaging system comprising:
    a spectral x-ray imaging device; and
    a spectral imaging phantom,
    wherein the spectral imaging phantom comprising a phantom body that comprises:
      a bulk of low attenuation material; a first insert positioned in the bulk, the first insert comprising a material comprising or corresponding to a material with a first Compton scatter and a first photo-electric absorption with respect to a scan energy of the spectral x-ray imaging device; and
      a second insert positioned in the bulk, the second insert comprising a material comprising or corresponding to a material with a second Compton scatter and a second photo-electric absorption with respect to the scan energy, wherein the first insert and the second insert have substantially the same attenuation profile with respect to the scan energy, and wherein a ratio of the first photo-electric absorption and the first Compton scatter is selected to be different from a ratio of the second photo-electric absorption and the second Compton scatter.

11. The spectral imaging system according to claim 10, wherein the spectral imaging phantom is embedded in a subject support of the spectral x-ray imaging device.

12. The spectral imaging system according to claim 10, wherein the x-ray imaging device is a spectral computed tomography imaging device.

13. A spectral imaging method comprising:
    inserting a spectral imaging phantom in an examination region of a spectral x-ray imaging device;
    performing a spectral x-ray scan comprising at last a scan of the spectral imaging phantom, thereby obtaining spectral imaging data of at least the spectral computed tomography phantom;
    using the obtained imaging data of the spectral computed tomography phantom as input for obtaining improved further imaging data of a subject of which a spectral computed tomography scan is performed subsequent to or simultaneous with the spectral computed tomography scan of the spectral imaging phantom;
    wherein the spectral imaging phantom comprising a phantom body that comprises: a bulk of low attenuation material; a first insert positioned in the bulk, the first insert comprising a material comprising or corresponding to a material with a first Compton scatter and a first photo-electric absorption with respect to a scan energy of the spectral x-ray imaging device; and a second insert positioned in the bulk, the second insert comprising a material comprising or corresponding to a material with a second Compton scatter and a second photo-electric absorption with respect to the scan energy, wherein the first insert and the second insert have substantially the same attenuation profile with respect to the scan energy, and wherein a ratio of the first photo-electric absorption and the first Compton scatter is selected to be different from a ratio of the second photo-electric absorption and the second Compton scatter.

14. The spectral imaging method according to claim 13, wherein the spectral imaging phantom is used as input for obtaining improved image data by using it as input for imaging data correction, for providing a recommendation and/or for further data processing.

15. The spectral imaging method according to claim 14, wherein the spectral scan of the subject is performed simultaneously with the spectral scan of the spectral phantom.

16. The spectral imaging method according to claim 13, wherein the subject is a patient and further imaging data is obtained of at least an area of interest in or on the patient.

17. The spectral imaging method according to claim 13, further comprising:
quantifying a crosstalk in material decomposition of the imaging data by application of a heuristic linear model to the image data, a set of free parameters of the heuristic linear model being optimized for a cost function;
correcting the obtained image data for the quantified crosstalk with the optimized free parameters; and, optionally,
determining at least one system parameter and use said at least one system parameter in the correction of the quantified crosstalk.

18. The spectral imaging method according to claim 13, further comprising:
comparing the obtained imaging data of the spectral phantom with reference imaging data, said reference data comprising theoretical data, data measured with other sources, previously measured data of a subject to be imaged, and/or data of the spectral phantom obtained during a previous scan of the spectral phantom, preferably a previous scan shortly after a latest calibration procedure; and
providing a recommendation for a special action, for instance a recommendation for performing a new calibration when a difference between the obtained imaging data and the imaging data obtained during or shortly after the latest calibration exceeds a predetermined threshold.

19. The spectral imaging method according to claim 13, further comprising:
reconstructing the imaging data by using the obtained imaging data of the spectral imaging phantom as input for a reconstruction algorithm, preferably an iterative reconstruction algorithm.

* * * * *